United States Patent [19]
Zeligs et al.

[11] Patent Number: 6,086,915
[45] Date of Patent: Jul. 11, 2000

[54] COMPOSITIONS AND METHODS OF ADJUSTING STEROID HORMONE METABOLISM THROUGH PHYTOCHEMICALS

[75] Inventors: Michael A. Zeligs, Boulder, Colo.; Irwin C. Jacobs, Eureka, Mo.

[73] Assignee: Bioresponse L.L.C., Boulder, Colo.

[21] Appl. No.: 09/053,180

[22] Filed: Apr. 1, 1998

[51] Int. Cl.$^7$ .................................................. A61K 9/66
[52] U.S. Cl. .................. 424/455; 424/439; 424/195.1; 424/456; 424/492; 514/323; 549/403
[58] Field of Search .................... 424/489, 439, 424/195.1, 442, 455, 456, 492, 497; 516/323; 549/403

[56] References Cited

U.S. PATENT DOCUMENTS

| | | | |
|---|---|---|---|
| 4,426,397 | 1/1984 | Schanze | 426/62 |
| 5,560,933 | 10/1996 | Soon-Shiong et al. | 424/489 |

FOREIGN PATENT DOCUMENTS 409100220  4/1997  Japan .

OTHER PUBLICATIONS

Lien et al, Hormone therapy and phytoestrogens. J. Clin. Pharm. Ther. vol. 21, 101–111, 1996.

Ruff et al. Inhibition of human estrogen synthetase (aromatase) by flavones. Sienec. vol. 225. 1032–1034, Sep. 7, 1984.

Bradlow et al. Indole–3–carbinol. a novel approach to breast cancer prevention. Annals of New York Academy of Sciences. vol. 768. 180–200, 1995.

Jellink et al. Influence of indole carbinols and growth hormone on metabolism of 4–androstenedione by rat liver microsomes. J. Steroid Biochem. Molec. Biol. vol. 46 (6). 791–798, 1993.

Liao et al. Selective inhibition of steroid 5alpha–reductase isozymes by Tea epicatechin–3–gallate and Epigallocatechin–3–gallate. Biochem. and Boiphys. Res. Comm. 214 (3). 833–838, 1995.

Hyrb et al. The effect of extracts of the roots of stinging nettle (*Urtica dioica*) on the interaction of SBHG with its receptor on Human Prostatic membranes. Planta Medica vol. 61. 31–32, 1995.

Bradlow et al., "Indole–3–carbinol A Novel Approach to Breast Cancer Prevention," *Annals New York Academy of Sciences* pp. 180–200 1995 vol. 768.

Hryb et al., 1995, "The Effect of Extracts of the Roots of the Stinging Nettle (*Urtica dioica*) on the Interaction of SHBG with its Receptor on Human Prostatic Membranes," *Planta Med.* 61:31–32.

Jellinck et al., 1993, "Influence of Indole Carbinols and Growth Hormone on the Metabolism of 4–Androstenedione by Rat Liver Microsomes," *J. Steroid Biochem. Molec. Biol.* 46(6):791–798.

Liao et al., 1995, "Selective Inhibition of Steroid 5α–Reductase Isozymes by Tea Epicatechin–3–Callate and Epigallocatechin–3–Callate," *Biochemical and Biophysical Research Communications* 214(3):833–838.

Michnovicz et al., 1994, "Dietary Cytochrome P–450 Modifiers in the Control of Estrogen Metabolism," *American Chemical Society* pp. 282–293.

Siess et al., 1996, "Flavonoids of Honey and Proplis: Characterization and Effects on Hepatic Drug–Metabolizing Enzymes and Benzo[α]pyrene–DNA Binding in Rats," *J. Agric. Food Chem.* 44:2297–2301.

Wattenberg et al., 1978, "Inhibition of Polycyclic Aromatic Hydrocarbon–induced Neoplasia by Naturally Occurring Indoles," *Cancer Reserach* 38:1410–1413.

*Primary Examiner*—Thurman K. Page
*Assistant Examiner*—Lakshmi Channavajjala
*Attorney, Agent, or Firm*—Pennie & Edmonds LLP

[57] ABSTRACT

The present invention relates to spray dried hydrophobic phytochemical chemopreventative compositions, a process for making such compositions and a method of using such compositions to adjust steroid metabolism in mammals. Typically, the hydrophobic dietary compositions of the present invention exhibit enhanced absorptivity when taken orally as a chemopreventative agent.

28 Claims, No Drawings

COMPOSITIONS AND METHODS OF ADJUSTING STEROID HORMONE METABOLISM THROUGH PHYTOCHEMICALS

TABLE OF CONTENTS

1. DESCRIPTION OF THE FIELD
2. BACKGROUND OF THE INVENTION
2.1. STEROID HORMONE STATUS AND DISEASE RISK
2.2. DIINDOLYL METHANE IS A CYP-INDUCING PHYTOCHEMICAL
2.3. DIM IS MORE STABLE THAN I3C
2.4. THE PHYTOCHEMICAL, CHRYSIN, INHIBITS CYP AROMATASE
2.5. THE ORAL BIOAVAILABILITY OF HYDROPHOBIC PHYTOCHEMICALS IS LIMITED
2.6. PRE-SYSTEMIC METABOLISM OF DIETARY SUBSTANCES
3. BACKGROUND ART
4. SUMMARY OF THE INVENTION
5. DETAILED DESCRIPTION OF THE INVENTION
5.1. FORMULATION FOR CYP ADJUSTMENT IN MALE AGING
5.2. FORMULATION FOR CYP ADJUSTMENT TO PROMOTE ESTROGEN BALANCE IN WOMEN
5.3. FORMULATION FOR CYP ADJUSTMENT TO PROMOTE PHYSICAL CONDITIONING
5.4. MAXIMIZING ACTIVE INGREDIENT ABSORPTION
6. EXAMPLES
6.1. EXAMPLE 1: INGREDIENTS OF AN ABSORPTION ENHANCING FORMULATION FOR DIM OR OTHER INSOLUBLE DIETARY INDOLES
6.2. EXAMPLE 2: DETAILED LIST OF PRODUCTION STEPS USED FOR THE MANUFACTURE OF PROCESSED DIM ("P-DIM")
6.3. EXAMPLE 3: INGREDIENTS OF AN ABSORPTION ENHANCING FORMULATION FOR CHRYSIN OR OTHER FLAVONOID
6.4. EXAMPLE 4: MANUFACTURE OF AN ABSORPTION ENHANCING PREPARATION FOR CHRYSIN ("P-CHRYSIN")
6.5. EXAMPLE 5: MANUFACTURE OF AN ABSORPTION ENHANCING FORMULATION OF BEE POLLEN
6.6. EXAMPLE 6: PREPARATION OF AN ABSORPTION ENHANCING FORMULATION OF THE COMBINATION OF PROCESSED DIM (P-DIM), PROCESSED CHRYSIN (P-CHRYSIN), *URTICA DIOICA*, AND AND GRAPEFRUIT CONCENTRATE FOR IMPROVING MALE HEALTH AND THE WELL-BEING OF THE PROSTATE GLAND
6.7. EXAMPLE 7: PREPARATION OF AN ABSORPTION ENHANCING FORMULATION OF THE COMBINATION OF PROCESSED DIM (P-DIM), SOY ISOFLAVONE CONCENTRATE, SAW PALMETTO CONCENTRATE, GREEN TEA EXTRACT AND GRAPEFRUIT CONCENTRATE FOR IMPROVING HORMONAL BALANCE IN WOMEN
6.8. EXAMPLE 8: PREPARATION OF AN ABSORPTION ENHANCING FORMULATION OF THE COMBINATION OF PROCESSED DIM, PROCESSED CHRYSIN, SAW PALMETTO CONCENTRATE, GREEN TEA EXTRACT, *URTICA DIOICA* EXTRACT AND GRAPEFRUIT JUICE CONCENTRATE FOR IMPROVING PHYSICAL CONDITIONING
6.9. EXAMPLE 9: EVIDENCE FOR ENHANCED ABSORPTION OF PROCESSED DIM IN ANIMALS
6.10. EXAMPLE 10: EVIDENCE THAT DIM MUST BE INCORPORATED IN PROCESSED FORM TO HAVE INCREASED BIOAVAILABILITY IN ANIMALS
6.11. EXAMPLE 11: EVIDENCE THAT DIM MUST BE INCORPORATED IN PROCESSED FORM TO HAVE INCREASED BIOAVAILABILITY IN HUMANS
6.12. EXAMPLE 12: EVIDENCE THAT PROCESSED CHRYSIN PROMOTES ENHANCED ABSORPTION
6.13. EXAMPLE 13: EVIDENCE THAT PROCESSED DIM, PROCESSED CHRYSIN AND URTICA DOICA PRODUCE A BENEFICIAL PATTERN OF STEROID METABOLISM IN HUMANS

1. Description of the Field

This invention relates to the use of particular groups of phytochemicals to promote a more beneficial metabolism of steroid hormones. The groups of phytochemicals useful for the invention are the indole alkaloid dietary phytochemicals and the flavonoid phytochemicals. Preparations of such phytochemicals are described which promote improved absorption of insoluble dietary substances to beneficially alter the activity of steroid metabolizing cytochrome P450 enzymes. This facilitated absorption of poorly soluble dietary substances amplifies useful dietary influences on steroid metabolism.

2. Background of the Invention

The superfamily of cytochrome P450 ("CYP") enzymes, inducible within a variety of cells, are able to metabolize poorly water-soluble hormones, drugs and chemicals. An individual's steroid hormone status is, therefore, a reflection of underlying CYP enzyme activity. CYP enzymes are the prime movers of steroid biosynthesis, activation and transformation to more water-soluble metabolites. Certain CYP enzymes have overlapping roles in biochemistry and are responsible for both the metabolism of steroids and the metabolism of structurally related substances of plant origin. Thus, the dietary intake of certain phytochemicals from plants, and man-made chemicals which resemble them, can influence the metabolism of steroid hormones which share the same CYP enzymes. Induction or inhibition of CYP enzyme activity can have a major impact on steroid hormone action since it is now known that much of the biologic activity of a given steroid resides with its specific metabolites, their relative concentration and biologic half-life (Michnovicz and Bradlow, "Dietary Cytochrome P-450 Modifiers In The Control Of Estrogen Metabolism," Chapter 23, in: Food Phytochemicals For Cancer Prevention I (Huang et al., eds., American Chemical Society, 1994).

2.1. STEROID HORMONE STATUS AND DISEASE RISK

Estrogen, or 17 beta-estradiol, is a steroid hormone of critical importance in reproduction, growth, development and metabolic well-being. It is important in maintaining health in both men and women. Changes in estrogen activity beginning in middle age have been associated with a spectrum of disease processes. Estrogen metabolism is dependent on a number of CYP enzymes, especially CYP 1A1 predominant in the liver, and CYP 1A2 and 1B1, present in the breast, uterus, ovary and skin. The level of induction of CYP 1A1, 1A2 and 1B1 varies according to hormonal status (e.g., thyroid hormone), dietary intake (e.g., indole phytochemicals) and exposure to environmental toxins (e.g., tobacco smoke and pesticides). Ratios of key estrogen metabolites reflect the degree of induction of specific estrogen hydroxylating, CYP enzymes. Additionally, the CYP enzyme aromatase ("CYP Aromatase") controls the intracellular estrogen levels by regulating conversion to estrogen from the androgens androstenedione and testosterone. CYP aromatase is particularly important in adipose or specialized connective tissue called stroma.

Observations as to the importance of specific estrogen metabolites began in the 1970's with the description of an increase in 16 0 H estrone in both men and women with systemic lupus erythematosus (Lahita et al., "Alterations Of Estrogen Metabolism In Systemic Lupus Erythematosus, Arthritis And Rheumatism," Vol. 22, No. 11 (1979)). This was followed by a definitive study in 1982 which revealed a similar increase in 16 0 H estrone in breast cancer patients (Schneider et al., "Abnormal Oxidative Metabolism Of Estradiol In Women With Breast Cancer," Proc. Natl. Acad. Sci. USA, Vol. 79, pp. 3047–3051 (1982)). This same observation was later extended to women with uterine cancer. (Fishman et al., "Increased Estrogen-16-Hydroxylase Activity in Women with Breast and Endometrial Cancer," Journal of Steroid Biochemistry And Molecular Biology, 20, No. 48, pp. 1077–81 (1984)).

Investigations of uterine disease correlated an increased 16 0 H estrone to 2 0 H ratio in cervical tissue to the extent of cervical dysplasia in cases of cervical intraepithelial neoplasia. (Sepkovic et al., "Estrogen Metabolite Ratios And Risk Assessment Of Hormone-Related Cancer, Assay Validation And Prediction Of Cervical Cancer Risk," Annals of the N.Y. Acad. of Science, Vol. 768, pp. 312–316 (1995)). The importance of disruption in this pathway of estrogen metabolism was further supported by the culture of human breast tissue from normal and cancerous sites which showed confirmatory increases in 16 hydroxylation in cancer specimens (Osborne et al., "Upregulation Of Estradiol c16 Hydroxylation In Human Breast Tissue: A Potential Biomarker Of Breast Cancer Risk," J. C. N. I. 85:23, pp. 1917–20 (1993)). A breast cancer cell study indicated a possible connection to environmental chemicals by demonstrating a shift in estrogen metabolism to more 16 0 H estrone production and less 2 0 H estrone production after exposure of cells to man-made pesticides (Bradlow et al., "Effects of Pesticides on the Ratio of 16/2-Hydroxyestrone: A Biologic Marker Of Breast Cancer Risk," Environmental Health Perspectives, 103(Suppl 7), pp. 147–50 (1995)).

The full importance of estrogen metabolism in determining estrogen-related disease is summarized in a recent review which explains the interaction between environmental chemicals ("xenoestrogens"), hormone metabolism and processes of DNA damage, now known to lead to breast cancer (Davis et al., "Medical Hypothesis: Bifunctional Genetic-Hormonal Pathways To Breast Cancer," Environmental Health Perspectives, 105(Supp. 3), pp. 571–576 (1997)). The weight of current evidence supports the concept that it is both the total cumulative exposure of tissues to estrogen and the pathway of estrogen metabolism which constitute estrogen-related disease risk.

The knowledge that specific CYP enzymes were responsible for the production of 2 0 H estrone triggered a re-examination of work from the 1970's which concerned induction of CYP enzymes by phytochemicals contained in dietary vegetables (Wattenberg and Loub, "Inhibition Of Polycyclic Aromatic Hydrocarbon-Induced Neoplasia By Naturally occurring Indoles," Cancer Research, 38, 1410–13 (1976)). This research showed that vegetables, plant extracts and particular phytochemicals were all able to prevent carcinogen-provoked cancer in animals. Wattenberg and Loub identified the inhibition of induced cancer by the indole group of dietary phytochemicals. This group of compounds shared a common, planar molecular structure which modulated CYP enzyme activity through the gene activation pathway known as the aryl hydrocarbon receptor system. Activity against carcinogen-induced cancer, or "chemoprevention," was linked to attributes of their heterocyclic molecular ring structure. Re-testing of this approach, led by H. Leon Bradlow at the Rockefeller University, established that indole-3-carbinol, a dietary indole from cruciferous vegetables, was indeed successful in shifting estrogen metabolism to favor 2 0 H estrone. (Bradlow et al., "Indole-3-Carbinol, A Novel Approach To Breast Cancer Prevention," Annals of the New York Academy of Science, 768:180–200 (1995)). Dietary influences on estrogen metabolism are now appreciated to be important modifiable factors for disease prevention.

2.2. DIINDOLYL METHANE IS A CYP-INDUCING PHYTOCHEMICAL

Hepatic and intestinal levels of CYP 1A1/1A2 enzyme are increased in rats and mice fed indole-3-carbinol ("I3C"), a dietary indole present in cruciferous vegetables. I3C supplementation in animals and humans has been shown to increase the 2-hydroxylation of estradiol, known to be due to activity of CYP IAI and 1A2 enzymes. Subsequent work revealed that acid condensation products formed from I3C during passage through the stomach possessed the CYP enzyme modulating effects. The acid condensation products, 3,3'-diindoly methane ("DIM") and 2,3-bis[3-indolylmethyl]indole, were detected in gastric contents and stomach tissue an hour after animals received an oral dose of I3C. (Stresser et al., "Mechanisms Of Tumor Modulation By Indole-3-Carbinol: Disposition And Excretion In Male Fischer 344 Rats," Drug Metabolism and Disposition, 23:9, pp. 965–75 (1995)). Subsequent work revealed the increased potency of DIM over I3C in influencing estrogen metabolism when DIM and I3C were both fed to rats and hepatic microsomal metabolism of estrogen measured (Jellinck et al., "Ah Receptor Binding Properties Of Indole Carbinols And Induction Of Hepatic Estradiol Hydroxylation," Biochemical Pharmacology, 45:5, pp. 1129–36 (1993)).

Recently cell culture observation demonstrated that DIM was able to support the cancer preventive behavior of apoptosis, i.e., programmed cell death (Ge et al., "3,3'-Diindoly methane induces Apoptosis In Human Cancer Cells," Biochemical And Biophysical Research Communications, 228, pp. 153–58 (1996)). The polycyclic ring structure of DIM, similar to other compounds known to effect the membrane-bound p-glycoprotein efflux mechanism, was shown to increase the effectiveness of chemotherapy drugs in multiply resistant cancer cells (Christensen and Leblanc, "Reversal Of Multidrug Resistance In Vivo By Dietary Administration Of The Phytochemical Indole-3-Carbinol," Cancer Research, 56, pp. 574–81 (1996)). Together, these observations suggest that DIM possesses both CYP-inducing activity and modulating effects on cell function that make it dually useful as a dietary supplement.

2.3. DIM IS MORE STABLE THAN I3C

I3C is now in use as a dietary supplement and has been reported to beneficially shift estrogen metabolism to favor 2 0 H estrone (Michnovicz et al., "Changes In Levels Of Urinary Estrogen Metabolites After Oral Indole-3-Carbinol Treatment In Humans," Journal of the Nat'l Cancer Inst., 89:10, pp. 718–23 (1997)). This use, for the chemoprevention of breast cancer and for the control of respiratory papilloma virus infection (Coll et al., "Treatment Of Recurrent Respiratory Papillomatosis With Indole-3-Carbinol," American Journal of Otolaryngology, 18:4, pp. 283–85 (1997)), requires a minimum dose of 300 mg per person per day (Wong et al., "A Dose-Response Study Of Indole-3-Carbinol For Breast Cancer Prevention," (submitted, 1998)). However, there are limitations to the use of I3C in dietary supplements preparations since I3C is unstable and subject to spontaneous breakdown accelerated by heat, light, moisture, or acidic environments. Shelf-life study of I3C revealed a loss of approximately 50% of the original I3C during aging conditions simulating a one month period (BioResponse New Dietary Ingredient FDA Filing, August (1997)). In addition, I3C demonstrates unpredictable transformation in vivo. During passage through the stomach I3C autoreacts into a family of condensation products consisting of double and triple molecules (dimers and trimers). One of the reaction products is indolocarbazole, a linear closed ring dimer of I3C which resembles dioxin in both structure and biologic activity (Bjeldanes et al., "Aromatic Hydrocarbon Responsiveness-Receptor Agonists Generated From Indole-3-Carbinol In Vitro and In Vivo: Comparisons With 2,3,7, 8-Tetrachlorodibenzo-P-Dioxin," Proc. Natl. Acad. Sci. USA, 88, pp. 9543–47 (1991)). This unpredictable formation of indolocarbazole in stomach acid makes supplementation with I3C of uncertain safety. The lack of shelf-life stability, spontaneous reaction of I3C with other dietary supplement ingredients and questionable reaction products formed in the stomach limit the usefulness of I3C as a dietary supplement ingredient.

Study of DIM by the inventors has revealed it to be entirely stable during passage through a simulated gastric environment (BioResponse New Dietary Ingredient FDA Filing, August (1997)). No indolocarbazole is generated in digestion, gastric acid, or during accelerated shelf-life conditions. DIM possesses desirable attributes as a CYP enzyme-inducer and is shelf stable. Therefore the need exists for a bioavailable formulation of DIM as well as related dimers and trimers, since hydrophobic substances like DIM are poorly absorbed.

2.4. THE PHYTOCHEMICAL, CHRYSIN, INHIBITS CYP AROMATASE

Flavones, analogous to dietary indoles, are natural plant compounds which effect estrogen activity and can prevent experimental cancer. 5,7-Dihydroxyflavone ("chrysin"), is a particular flavone found in extracts of the passion flower (Passiflora corerula) and in bee pollen or propolis. This dietary substance has been shown to inhibit CYP Aromatase activity in cell culture and cell-free microsomes (Campbell and Kurzer, "Flavonoid inhibition of aromatase enzyme activity in human pre-adipocytes," J. Steroid Biochem. Molec. Biol, 46:3, pp. 381–388 (1993) and Kellis and Vickery, "Inhibition of human estrogen synthetase (aromatase) by flavones," Science, 225, pp. 1032–1034 (1984)). Modulation of aromatase activity is important since this CYP enzyme controls conversion from androgens to estrogen in peripheral tissue such as fat. With aging, body composition shifts to favor an increased proportion of fat to lean tissue such as muscle. As a result, there is an increasing production of estrogen from testosterone and the "adrenal androgen," dehydroepiandrosterone (DHEA), in both men and women with advancing age. Anti-CYP aromatase activity by dietary flavones and related isoflavones is now believed to provide an important source of protection from estrogen-related disease by limiting the metabolic conversion of androgens to estrogens.

Despite the significant anti-aromatase activity demonstrated by chrysin in cell-free and cell culture studies referenced above, low oral bioavailability of flavones has been cited as a problem with regard to their potential usefulness as dietary supplements (Kuhnau, "The flavonoid. A class of semi-essential food components: their role in human nutrition," World Rev. Nutr. Diet, 24, pp. 117–191 (1976)). When studied as to its physico-chemical characteristics, chrysin was shown to be extremely hydrophobic with a water solubility of only $2.8 \times 10^4$ moles/liter (Masarova et al., "Solubilization of chrysin by a non-aromatic amine oxide," Pharmazie, 44, H 12, pp. 865–866 (1989)). Therefore, the need exists for improved bioavailability for dietary supplement formulations of chrysin in order to derive benefit from its CYP Aromatase inhibiting action.

2.5. THE ORAL BIOAVAILABILITY OF HYDROPHOBIC PHYTOCHEMICALS IS LIMITED

Efficient oral uptake of phytochemicals is necessary to provide adequate systemic tissue levels to induce protective CYP enzymes. Water insoluble or hydrophobic dietary substances must overcome multiple barriers to their digestive absorption. These barriers include: resistance to emulsification within the lipid-based intestinal micelles; immediate "pre-systemic metabolism" upon entering enterocytes lining the small bowel; and return to the gut lumen by action of the p-glycoprotein efflux pump which actively extrudes many hydrophobic substances from within enterocytes. Formulations which encourage emulsification into micelles, reduce enterocyte metabolism and increase uptake of substances into chylomicrons can improve the bioavailability of hydrophobic substances. Increased chylomicron flux and passage of substances into the lymphatic flow will bypass some of the "first pass" hepatic metabolism effecting water-soluble substances or water-soluble metabolites generated by enterocytes.

Initial development of a laboratory synthesis for DIM in the 1950's revealed the substance to be highly water insoluble. (Leete and Marion, "The Hydrogenolysis Of 3-Hydroxymethylindole And Other Indole Derivatives With Lithium Aluminum Hydride," Canadian J. of Chemistry, 31:9, pp. 775–84 (1953)). Cell culture studies revealed DIM to be a powerful CYP enzyme-inducer when added directly to cultured liver cells. (Wortelboer et al., "Effects of Indole-3-Carbinol On Biotransformation Enzymes In The Rat: In Vivo Changes In Liver And Small Intestinal Mucosa In Comparison With Primary Hepatocyte Cultures," Food Chem. and Toxicology, 30:7, pp. 589–99 (1992)). However, when DIM was either added to the diet or injected intraperitoneally in rats a markedly diminished effect was noted. A loss of activity was noted below 5 mg per kg, even when DIM was administered in sesame oil, an uptake enhancing vehicle. Enzyme inductive effects were noted down to 0.3 mg per kg when DIM was injected intraperitoneally (Jellinck et al., "Ah Receptor Binding Properties of Indole Carbinols and Induction of Hepatic Estradiol Hydroxylation," Biochemical Pharmacology, 45:5, pp. 1129–36 (1993)). When included in the diet and mixed with feed in a separate study, large doses of DIM failed to induce CYP enzymes in colonic epithelium whereas a powerful inductive activity was demonstrated for water-soluble I3C (McDannell and McLean, "Differential Induction of Mixed-Function Oxidase (MFO) Activity in Rat Liver and Intestine by Diets Containing Processed Cabbage: Correlation with Cabbage Levels of Glucosinolates and Glucosinolate Hydrolysis Products," Food Chem. and Toxicology, 25:5, pp. 363–68 (1986)). This study demonstrates a failure of absorption of DIM in pharmacologic dosage.

When the bioavailablity of chrysin was investigated as part of a feeding study, no CYP-related effects were noted in rat livers despite two weeks of oral intake at 300 mg/kg of body weight. Intake of Tangeretin, a more lipid-soluble flavone, was associated with CYP induction (Siess, MH, Guillermic, M, LeBon, AM, Suschetet, M, "Induction of monooxygenase and transferase activities in rat by dietary administration of flavonoid," Xenobiotica, 19:12, pp. 1379-13–86 (1989)). The need thus exists to develop specific formulations, suitable for use as dietary supplements, to facilitate the oral absorption of useful, but insoluble dietary substances.

2.6. PRE-SYSTEMIC METABOLISM OF DIETARY SUBSTANCES

The bioavailability of a number of hydrophobic phytochemicals can be limited by metabolism within the enterocyte cell layer lining the digestive tract. This "pre-systemic" metabolism involves the CYP 3A4 class of cytochrome enzymes. CYP 3A4 enzyme activity is linked to the extrusion of hydrophobic compounds from the enterocyte back into the gut lumen through activity of the p-glycoprotein membrane efflux pump (Wacher and Bennet, "Overlapping Substrate Specificities and Tissue Distribution of Cytochrome p450 3a and P-Glycoprotein: Implications for Drug Delivery and Activity," in Cancer Chemotherapy, Molecular Carcinogenisis, 13: pp. 129–34 (1995)). Since essential oils from various plant sources possess CYP 3A4 inhibitory activity, co-administration of oils in emulsions with hydrophobic drugs has been developed in a system for increasing the uptake of certain drugs by reducing the activity of the p-glycoprotein membrane efflux pump (U.S. Pat. No. 5,665,386). A number of substances of dietary origin are both substrates for CYP 3A4 enzymes and preferentially selected for extrusion from the cell by the p-glycoprotein pump. Because of structural similarities to various drugs it is probable that the uptake of dietary substances, like DIM and chrysin, are also effected by the activity of CYP 3A4 enzymes and p-glycoprotein.

However, DIM has proven to be unique with regard to the enterocyte system of selective metabolism and extrusion of substances back into the gut lumen. Inhibition of the function of the p-glycoprotein has been noted in cell culture and in vivo following DIM administration. Thus, DIM reduces the effectiveness of the system in eliminating other hydrophobic compounds (Christensen and Leblanc, "Reversal of Multidrug Resistance In Vivo by Dietary Administration of the Phytochemical Indole-3-Carbinol," Cancer Research, 56, pp. 574–81 (1996)). This resulted in the increased effectiveness of chemotherapeutic compounds in multiply resistant cancer cells. Use of a molecular probe demonstrated direct interaction of DIM with the p-glycoprotein membrane structure. Therefore, DIM possesses the special attribute of being able to block its own efflux after having gained access to the enterocyte. So, if formulated to overcome the solubility barrier to absorption within enterocytes, DIM would stimulate its own further systemic uptake and bioavailability as well as the bioavailability of other substances subject to p-glycoprotein efflux.

Apart from DIM and essential oils, two other classes of compounds have been observed to inhibit CYP 3A4 and p-glycoprotein linked bioavailability. The first involves administration of surfactants which effect membrane fluidity and block p-glycoprotein efflux activity through subtle changes in the lipid protein interaction upon which p-glycoprotein depends. This knowledge has been developed into a means of co-administering surfactants with chemotherapeutic drugs to treat drug resistant cancer (U.S. Pat. No. 5,591,715).

Secondly, it has also been noted that natural substances found in grapefruit juice effectively block CYP 3A4 activity to a range of its substrates, promoting the enhanced absorption of various drugs such as quinidine, cyclosporine and felodipine (Lown et al., "Grapefruit Juice Increases Felodipine Oral Availability In Humans By Decreasing Intestinal CYP 3A Protein Expression," Journal of Clinical Investigation, 99:10, 2545–53 (1997)). Since DIM is structurally similar to quinidine, it would be advantageous to develop a formulation of DIM which utilized grapefruit juice and blocked the activity of CYP 3A4. This would further encourage the absorption of DIM and other co-administered dietary substances like flavones and isoflavones. It would also be beneficial to have a formulation which inhibited both CYP 3A4 activity and directly blocked the p-glycoprotein pump system. This is possible through the co-administration of surfactants known to specifically interrupt the activity of p-glycoprotein through membrane effects as described. Ideally, the facilitated uptake due to these effects is transient, allowing facilitated uptake of compounds intentionally co-administered with grapefruit concentrate and surfactant. This would be followed by a return of CYP 3A4 function within a matter of hours allowing the enterocyte barrier to resume its protective function of excluding other unselected and potentially toxic hydrophobic compounds. Preliminary pharmacokinetic study of the effect of grapefruit juice concentrate indicates reversal of its effect within 8 to 12 hours (Ameer, B. and Weintraub, R. A., Clinical Pharmacokinetics, 33(2):103–21 (1997)).

3. BACKGROUND ART

Art formulation technology has addressed the need for improving the absorption of hydrophobic substances. The focus of this work has concerned the use of polyethylene glycol (PEG) as a surfactant, creation of microsdispersions to reduce particle size and the use of spray drying techniques to form discrete particles.

The early work with PEG is exemplified by the patent by Riegleman and Chiou which included the intimate association of poorly soluble drug with soluble PEG carriers for enhanced absorption (U.S. Pat. No. 4,151,273). The usual technology in such formulations was to combine a heated mixture of PEG or polyvinylpyrrolidone with poorly soluble drug, followed by subsequent cooling to form a "solid solution" of dispersed drug. This solid mixture or dispersion was subsequently ground into a fine powder for tableting. The enhancements of this technology concerned the preparation of various liquid or oil based dispersions or emulsions of insoluble substances for oral administration. The technology for the creation of finer particle size in dispersions was subsequently described for excipient systems of lipids and surfactants promoting reduced particle size (U.S. Pat. No. 4,880,634). The addition of free fatty acids and phospholipids to emulsion forming technology was then described for better compatibility with intestinal micelles (U.S. Pat. No. 5,314,921). More complex emulsions and multiple emulsions in digestible oil were most recently described as variations on this theme (U.S. Pat. Nos. 5,645,856 and 5,583,105).

The technology of mixing hydrophobic substances in coating materials, described by Sair and Sair (U.S. Pat. No.

4,230,687), has been the basis for creating various forms of stable microdispersions using mechanical mixing in various polymeric encapsulating materials such as starch, gum or protein. However, this technique requires thick mixtures of starch in order to preserve the discreet microdispersion particles. Enhancement of oral uptake was achieved for dipyridamole by the creation of an amorphous, non-crystalline mixture with polyvinylpyrrolidone as the emulsifier, followed by spray drying the mixture (U.S. Pat. No. 4,610,875). The process of spray drying an emulsion of lecithin, organic oil and a non-ionic poloxamer surfactant was developed for the creation of shelf stable flavorants in the food industry (U.S. Pat. No. 5,362,425). Improved particle formation for insoluble drugs was later described which included the use of carboxylic acid esters of PEG, like vitamin E succinate PEG 1000 ("TPGS"), as emulsifying agents and a coating material mixed prior to spray drying to form particles (U.S. Pat. No. 5,430,021).

TPGS has been independently explored as both a water-soluble form of vitamin E and as a means of creating liquid emulsions in combination with hydrophobic drugs or vitamins. This use has provided for applications to increase the uptake of vitamin D and poorly soluble drugs such a cyclosporine (Argao et al., "d-α-Tocopheryl Polyethylene Glycol-1000 Succinate Enhances the Absorption of Vitamin D in Chronic Cholestatic Liver Disease of Infancy and Childhood," Pediatric Research, 31:2, 146 (1992)). TPGS and related food grade PEG esters have proved to be useful as a means of increasing the absorption of the esterified vitamin E as well (U.S. Pat. No. 5,179,122). Other formulations of TPGS in combination with non-esterified vitamin E have been developed by mixture of TPGS with flow enhancing agents and spraying (U.S. Pat. No. 5,234,695). In these uses TPGS had been employed as an emulsifying agent which improves intestinal absorption. However, this function is not unique to TPGS as use of the unrelated Milk Fat Globule Membrane lipid fraction from cow's milk has shown, in which an emulsion increased the uptake of cyclosporine to a similar degree (Sato et al., "Enhancement of the intestinal absorption of a cyclosporine derivative by milk fat globule membrane," Biol. Pharm. Bull. 17(11), pp. 1526–1528 (1994)). The most recent work with TPGS explored the mechanism by which this PEG ester increased the bioavailability of cyclosporine.

Measurement of cyclosporine metabolites revealed that TPGS did not effect the action of CYP 3A4 enzymes and instead implied that in addition to enhanced solubilization there must be a second mechanism by which TPGS acts in order to account for the degree of enhanced drug uptake observed. It was speculated that this mechanism may involve inhibition of the p-glycoprotein pump. (Chang et al., "The effect of water-soluble vitamin E on cyclosporine pharmacokinetics in healthy volunteers," Clinical Pharmacology & Therapeutics, 59:297–303 (1996)).

Based on the evidence supporting the use of dietary phytochemicals to shift estrogen metabolism to more beneficial metabolites like 20 H-estrone, the need exists to develop safe and effective formulations for dietary supplements. The preferred dietary phytochemicals for enzyme induction, like DIM and chrysin, are highly insoluble and subject to anti-absorptive mechanisms which limit oral bioavailability. Therefore, the need exists for formulation technology and preparations of phytochemical combinations which overcome the barriers to their absorption.

4. SUMMARY OF THE INVENTION

Specialized nutrient preparations and formulation techniques using plant-based compounds have been developed for use as dietary supplements. These preparations are used in dietary approaches to maintain and restore hormonal balance. Such preparations overcome the poor solubility and low bioavailability of dietary substances when ingested as supplements in humans and animals. New formulation technology has been developed which permits the creation of a microdispersion of insoluble dietary substances in association with polyethylene glycol esters and natural surfactants. This microdispersion is captured within particles of starch through a spray-drying process. The result is a fine powder, with each particle containing microparticles of the solidified dietary substance in amorphous, non-crystalline complexes. The preparation stabilizes the dietary substance, providing a long shelf-life and the ability to combine with other dietary supplement ingredients. Most importantly these preparations enhance the absorption of insoluble dietary substances when ingested, providing for effective treatment with a low dose for long-term users.

The enhanced uptake and bioavailability of the preparations have been tested in animal and human experiments. The results establish a significant advantage over the same substances in an unprocessed, crystalline state. The preparations constitute a method for safely delivering poorly soluble nutrients which induce specific CYP enzymes to promote estrogen balance. These preparations improve the absorption of plant substances like the plant indole, DIM and the plant flavone chrysin. The preparations have proven useful in adjusting estrogen metabolism when used orally in mammals. These dietary substances have been shown to induce safer metabolism of carcinogens and are therefore useful, when prepared according to the present invention, as chemopreventive formulations.

5. DETAILED DESCRIPTION OF THE INVENTION

The present invention concerns the formulation and use of nutrient preparations for enhanced absorption of highly insoluble, hydrophobic phytochemicals. The ultimate objective of the invention is to promote more beneficial steroid hormone metabolism. This is accomplished with formulations of dietary substances whose facilitated absorption adjusts CYP steroid metabolizing activity. Preparations are based on the steps of co-dissolving the dietary substances in an appropriate solvent, an emulsifier (e.g., vitamin E succinate PEG ester) and phospholipids, followed by the creation of a stable microdispersion in water-soluble matrix-forming agent. Amorphous complexes of microdispersed dietary substances are then co-precipitated within carrier particles formed by spray drying. These formulations, with active dietary substances residing in microparticles, promote enhanced absorption when dissolved and emulsified within the small intestine of a human or animal.

Natural indoles, such as DIM, or flavonoid, such as chrysin, are examples of dietary substances of plant origin that demonstrate negligible solubility in water (2.5 and 0.7 µg/ml, for DIM and chrysin, respectively) and minimal solubility in oil (100 and 50 µg/ml, for DIM and chrysin, respectively). Other dietary substances which can be used according to the invention include, but are not limited to linear tri-indole([2-(indol-3-ylmethyl)-indol-3yl]indol-3-ylme thane), cyclic tri-indole (5,6,11,12,17,18-hex-hydrocyclononal[1,2-b:4,5-b':7,8-b ]:triindole), linear di-indole (1-(3-hydroxymethyl)indolyl-3indolymethane, tectochrysin (5-hyroxy,7-methyletherflavone), nepetin (5,3', 4'-trihydroxy-6-methoxyflavone), tangeretin (5,6,7,8,4'-pentamethoxyflavone), tricetin (5,7-dihydroxy-3'4',5'-trimethoxyflavone), tricin (5,7,4'trihydroxy-3',5'- dimethoxyflavone), amentoflavone, pinocembrin (5,7-dihydroxyflavanone), narigenin (5,7,4'trihydroxyflavanone), biochanin A, genistein, daidzein, bee pollen or propolis.

The development of absorption enhancing formulations for oral use has been necessary in order to take advantage of the health promoting effects of such substances which are now available in synthetic, concentrated forms. Because of the unique physico-chemical characteristics of hydrophobic phytochemicals like DIM and chrysin, new formulation approaches have been developed to improve their oral bioavailability. The formulation technology developed is identified by processing steps which allow for the re-distribution of insoluble ingredients to surfactant-rich microparticles. The focus of this processing has been the creation of a solid dispersion of microparticulates contained within a larger matrix of starch particles. These 10 micron starch particles contain the microparticulates which consist of an amorphous solid phase of a mixture of hydrophobic phytochemicals such as DIM or chrysin together with solubilizing emulsifier (e.g., vitamin E succinate polyethylene glycol 1000; vitamin E succinate Polyethylene glycols with polyethylene glycol (with a molecular weight range of 400–2000); other polyethylene glycol esters such as those formed by fatty acids such as oleic acid or stearic acid; polyvinylpyrrolidones; polyvinylpolypyrrolidones; Poloxamer 188, Tweens; or Spans) and a phospholipid.

The formulation process described employs a new approach to particle size reduction through formation of an optimized microdispersion in an aqueous phase which is then converted, through spray drying, to a free flowing powder comprising the water soluble matrix containing the embedded microparticles. In the process, the solubility enhancing activity of polyethylene glycol esters is adapted for maximal dissolution of DIM or chrysin in a warm (from 30° C. to 90° C.) mixture of food-compatible solvents, phospholipid and TPGS.

Possible solvents include hexanol, ethanol, butanol, heptanol, 2-methyl-1-pentanol, various ketone solvents that would be acceptable in foods such as methyl ethyl ketone, acetone and others, propylene glycol and certain ester solvents such as ethyl acetate.

Possible phospholipids can include the constituents of lecithins (e.g., phosphatidyl serine, phosphatidyl inositol and phosphatidyl glycerol); phospholipid derived from soy; phospholipid derived from milk-fat globule membrane ("MFGM"); dioleoyl phosphatidylcholine; phoshatidylglycerol; dioleoylphosphatidylglycerol; dimyristoylphosphatidylcholine; dipalmitoylphosphatidylcholine; phosphatidylethalolamines; phosphatidylserines; sphingomyelins; poly gylcerol esters; or ethoxylated castor oil. The phospholipid is added to the TPGS/solvent mixture to cause reduction in size of the dispersed phase after mixing with water. High shear mixing of this organic phase causes either dissolution, or the production of an extremely fine suspension of the DIM, chrysin, other phytochemical, or mixture of phytochemicals in an intimate mixture with the solubilizing emulsifier (e.g., TPGS) and phospholipid.

The ratio of the mixtures were refined for each phytochemical to maximize the stability of the emulsion. The ratio of TPGS to either DIM or chrysin should be in the range of 0.5:1 to 1.5:1. A ratio of 1:1 is preferred. The starch should be from 25% to 75% of the total mass of components and is preferably in a ratio of 0.8:1 to 1.5:1 with the TPGS. The emulsifiers, which can include either or both phosphatidyl choline and bile salts (e.g., sodium cholate, deoxycholate, taurocholate, etc.) should be from 1% to 10% of the total mass, with 3% to 5% preferred. The solvent should be at a mass ratio of 0.5:1 to 5:1 with the active ingredient (e.g., chrysin or DIM).

Next this "melt" of extracted hydrophobic components is homogenized in a water based solution of starch or other encapsulator (e.g., modified starch such as Capsul™ Starch from National Starch, Inc.; methylcellulose; hydroxypropyl methylcellulose; hydroxyethylcellulose; hydroxypropylethylcellulose; pectin; gum arabic; gelatin; or other polymeric matrix-forming preparation known to those skilled in the art, soluble in water and, suitable for spray drying). This step creates a microdispersion which resists coalescence and maintains discrete microparticles of TPGS, phospholipid and hydrophobic phytochemical (such as DIM or chrysin) maintaining approximately a 5 micron or smaller size range. In a preferred embodiment, the microparticle is 2 microns or less. In a particularly preferred embodiment, the microparticle is 1 micron or less. Subsequently, through the process of spray drying, solvent is eliminated and the carrier (e.g., TPGS and phosphatidyl choline) is precipitated to form "microparticles" within larger starch particles. The amorphous, non-crystalline microparticles are easily released from the starch particles upon contact with intestinal fluids. Following this, the microparticles are compatible and coalesce with intestinal phospholipid/bile salt micelles.

Following spray drying, the solidified microparticles of co-precipitated solubilizing emulsifier, phospholipid and hydrophobic phytochemical are in an easily emulsifiable form. In the intestine, the presence of TPGS, for example, results in surfactant activity which facilitates incorporation of phytochemical-rich micelles into enterocyte lipid membranes. The intimate association of phytochemicals in microparticulate complexes with TPGS provides for advantageous uptake through the intestinal surface. As described previously for PEG diesters and the Cremophor class of surfactants, (Buckingham et al., "Reversal Of Multi-drug Resistance In Vitro By Fatty Acid—PEG Diesters," International J. of Cancer, v. 65, pp. 74–79 (1996)), action of the TPGS within the membrane is able to intentionally impair p-glycoprotein efflux function. The TPGS and DIM are presumed to act synergistically to inhibit the P-glycoprotein mediated "efflux pump" reducing return of the indole or other phytochemical from intestinal enterocyte cells to the intestinal lumen. Formulations made in this manner resulted in unexpectedly high bioavailabilty of DIM. Also, co-administered compounds specific for inhibition of the CYP 3A4 enzyme system within enterocytes can be added to the preparation in the compounding step. This "anti-CYP 3A4" component is exemplified by grapefruit juice concentrate or sulfophorane from broccoli, previously shown to enhance absorption of CYP 3A4 substrates by inhibiting metabolism of substances once inside enterocyte cells.

The unexpected action of TPGS as both an emulsifier and an efflux pump inhibitor in combination with phytochemicals which also inhibit p-glycoprotein and CYP 3A4 enzymes resulted in formulations of dietary substances and surfactant which stimulate their own uptake through synergistic action. Each preparation described in the ensuing examples increases bioavailability of hydrophobic dietary substances by the combination of three specific actions: i) enhanced incorporation into intestinal micelles and penetration of enterocytes through the action of TPGS and phospholipids; ii) inhibition of p-glycoprotein mediated efflux back into the intestinal lumen through combined effects of TPGS and DIM; and iii) inhibition of the metabolism of delivered hydrophobic substances by CYP 3A4 through action of co-administered grapefruit juice concentrate or phytochemical like sulfophorane or DIM. Absorbed phytochemicals are thus passed into lymphatic and portal circulation in increased concentration, as compared to administration without processing into TPGS/phospholipid microparticles and co-administration with a CYP 3A4 inhibitor like grapefruit juice concentrate or sulfophorane.

Applications of the formulation technology exist for pure synthetic phytochemicals like DIM and chrysin, and for natural product preparations such as soy bean concentrates, extracts of the Stinging Nettle (*Urtica dioica*) and preparations of bee pollen or propolis. In each case the formulation process segregates lipid soluble phytochemical components from water soluble components in the final product. The use of hexanol, propylene glycol, or other solvent system in the formulation process partitions lipid compatible substances into the microparticles of TPGS and phospholipid, leaving the water soluble substances to reside in the starch or other carrier forming matrix material. In the case of *Urtica dioica*, for example, lipid soluble substances like hydroxyoctadecanoic acid, possessing anti-aromatase activity, are segregated into the TPGS/phospholipid complexes while the more water soluble phytochemicals are segregated to the starch matrix. The bioavailability of the more hydrophobic phytochemicals is increased by the process of formulation.

Bee pollen and propolis represent natural products in which flavones, including chrysin, are concentrated in a mixture of pollen granules and plant resins (Siess et al., "Flavonoids of Honey and Propolis: Characterization and effects on hepatic drug-metabolizing enzymes and benzo[a]pyrene-DNA binding in rats", J. Agric. Food Chem., 44:8, pp. 2297–2301 (1996)). Since the CYP inducing activity of dietary propolis is superior to that of flavonoid extract from propolis, processing of bee pollen (closely related to propolis) according to the present formulation technology was undertaken to provide a useful preparation for dietary supplementation. The addition of a grinding step and dissolution of the complex mixture in a propylene glycol based solvent system permitted microencapsulation of the water insoluble flavone components in association with TPGS. Other useful components of the bee pollen, including the cinnamic acids, were similarly associated with TPGS. The advantage of this approach is that chrysin or other useful flavone can be concentrated by providing bees with a plant source of known flavone content, such as sunflowers, obviating the need for preprocessing purification or synthetic synthesis of chrysin. Formulations which combined processed preparations of DIM and chrysin permitted enhanced effectiveness in balancing estrogen metabolism by allowing simultaneous delivery of substances which induce CYP1A1/1A2 and inhibit CYP aromatase.

Use of the components described above permitted formulation of dietary supplements which modified CYP activity to promote more beneficial estrogen metabolism in three specific conditions. These include the promotion of prostate health and limitation of estrogen accumulation associated with male aging, the adjustment of estrogen metabolism in women to promote 20 H estrone formation and maintain estrogen levels, and promotion of a high testosterone to estrogen ratio to promote physical conditioning in athletes.

5.1. FORMULATION FOR CYP ADJUSTMENT IN MALE AGING

This formulation combined CYP enzyme modulating effects of DIM, chrysin and the natural product *Urtica dioica* to intervene in estrogen-related aspects of male aging or the "Andropause." In distinction from the traditional view of male aging as primarily related to decreasing bioavailable testosterone, the present invention introduces the concept of male aging as propelled by estrogen accumulation and diminished estrogen clearance. Use in this formulation of bioavailable DIM increased the CYP enzymes responsible for metabolism of estrogen to 20H-estrone and 2Methoxyestrone. The formulation's action with DIM, in conjunction with bioavailable chrysin, reduced both the precursor pool of androstenedione (Jellinck et al., "Influence of indole carbinols and growth hormone on the metabolism of 4-androstenedione by rat liver microsomes," J. Steroid Biochemistry and Molec. Biol., 46:6, pp. 791–798 (1993)) and the activity of the CYP Aromatase enzyme system to further reduce tissue levels of estrogen. The addition of extracts from *Urtica dioica* provided further anti-aromatase activity in the form of Hydroxy-octadecanoic acid as well as a water-soluble component which specifically impedes estrogen activation of Sex Hormone Binding Globulin (SHBG) (Hryb et al., "The effect of extracts of the roots of the Stinging Nettle (*Urtica dioica*) on the interaction of SHBG with its receptor on human prostatic membranes," Planta Medica, 61, pp. 31–32 (1995)). These combined activities on steroid metabolism and action reduce estrogen driven stimulation of the prostate gland, reduce estrogen-related increases in SHBG synthesis by the liver and promote increased bioavailable testosterone.

5.2. FORMULATION FOR CYP ADJUSTMENT TO PROMOTE ESTROGEN BALANCE IN WOMEN

A formulation for women was developed using bioavailable DIM, Saw Palmetto extract, green tea extract and phytoestrogen concentrate (e.g. isoflavone concentrate from soy). In contrast to the formulation for men, this combination of CYP enzyme modulating phytochemicals preserves and supports estrogen levels. DIM induction of CYP 1A1/1A2 enzymes assures metabolism of estrogen in the safe direction of 20 H estrone, thereby increasing the 20 H estrone to 160 H ratio. The action of Saw Palmetto and green tea extracts, not previously used in women's supplements, is to block 5 alpha reductase and thereby preserve androstenedione (Liao, S. and Hiipakka, R. A., Biochem. Biophys. Res. Comm., 214(3):833–38 (1995)). Androstenedione, derived directly from DHEA, is a substrate for CYP Aromatase and an important source of estrogen in older women. This new use of Saw Palmetto in women, and avoidance of chrysin or other aromatase inhibitor, preserves the activity of CYP aromatase and maintains estrogen derived from androgen precursors. The use of soy isoflavones in the formulation provides activated metabolites, especially Equol, Daidzein and Genistein, which have predominantly estrogenic action. Higher estrogen levels and soy isoflavones support bone mineralization and increase SHBG production by the liver. SHBG in women is protective for breast and uterine tissue, preventing excessive stimulation by unbound estrogen. By adjusting the balance of CYP enzyme activity, this formulation increases the safety of Hormonal Replacement Therapy (HRT) with estrogen, progesterone and DHEA. In an alternative mode, a concentrate of lignans which produce the estrogenic metabolites, Enterodiol and Enterolactone, may be substituted for soy isoflavone concentrate.

5.3. FORMULATION FOR CYP ADJUSTMENT TO PROMOTE PHYSICAL CONDITIONING

A dietary supplement formulation promoting conditioning and muscle mass in athletes was developed based on a combination of bioavailable DIM, bioavailable chrysin, Saw Palmetto extract, and green tea extract. An elevated testosterone to estrogen ratio was promoted through the CYP enzyme modulating effects of these combined phytochemicals. The action of chrysin together with Saw Palmetto and green tea extracts preserved androstenedione levels by limiting metabolism through CYP aromatase and 5 alpha reductase. Higher levels of androstenedione result in increased conversion to testosterone, especially if accompanied by additional supplementation with DHEA and androstenedione. Bioavailable DIM lowered circulating estrogen due to increased clearance through 20 H estrone and 2 methoxyestrone. Together with aromatase inhibition by chrysin, the DIM effect helped preserve pituitary LH secretion, since estrogen and aromatase act to inhibit this secretion. Higher LH levels promoted greater testosterone production in men. This combination of dietary substances shifts steroid metabolism to favor an elevated testosterone to estrogen ratio especially in muscle cells. To enhance the CYP modulating effects of the formulation, *Urtica dioica* extract containing the aromatase inhibiting principle, Hydroxy-octadecanoic acid, was added to the formulation. When combined with exercise and resistance training, anabolism and muscular hypertrophy resulted from dietary supplementation with the formulation.

5.4 MAXIMIZING ACTIVE INGREDIENT ABSORPTION

Each of the above formulations additionally included either grapefruit juice concentrate or cruciferous vegetable extract containing sulfophorane to limit the action of intestinal CYP 3A4 "pre-systemic metabolism" of phytochemical components. Uptake enhancing effects were also derived from the action of TPGS and DIM when they were present. The preferred practice of dietary supplementation with the above formulations also involves administering the supplements with small amounts of fatty food. This further encourages uptake of lipid-soluble phytochemicals by increasing the rate of enterocyte chylomicron formation. Increased chylomicron formation and flux into the lymphatic flow improves the total absorption of substances by the lymphatic route avoiding "first-pass" metabolism by the liver.

Examples follow to demonstrate the bioavailability enhancing action of the ingredients and formulations as described. The delivery system technology was studied and shown to increase the absorption of DIM or chrysin. The strong CYP enzyme-inducing activity of DIM was used to demonstrate the advantage of processed DIM over crystalline DIM alone. This approach has been used in animals by feeding either crystalline DIM or processed DIM and by directly measuring CYP enzyme levels in liver and other tissues. In humans, the same comparisons were made using repeated assays of steroid metabolites in urine instead of direct tissue analysis. Since steroid metabolites are directly tied to tissue levels of CYP enzymes and activity, the use of urine studies was used as indirect but reflective measurement of changes in tissue CYP activity.

6. EXAMPLES

6.1. EXAMPLE 1: INGREDIENTS OF AN ABSORPTION ENHANCING FORMULATION FOR DIM OR OTHER INSOLUBLE DIETARY INDOLES

Ingredient List:

1. About 10 to about 40 percent by weight of a dietary indole selected from the following, alone or in combination: pure diindolylmethane (3,3'-diindolylmethane), linear tri-indole([2-(indol-3-ylmethyl)-indol-3yl]indol-3-ylme thane), cyclic tri-indole (5,6,11,12,17,18-hexhydrocyclononal[1,2-b:4,5-b':7,8-b ]:triindole), and linear di-indole (1-(3-hydroxymethyl)indolyl-3indolymethane.

2. About 10 to about 40 percent by weight of the following, alone or in combination: vitamin E succinate polyethylene glycol 1000; vitamin E succinate Polyethylene glycols with polyethylene glycol (with a molecular weight range of 400–2000); other polyethylene glycol esters such as those formed by fatty acids such as oleic acid or stearic acid; polyvinylpyrrolidones; polyvinylpolypyrrolidones; Poloxamer 188, Tweens; or Spans.

3. About 5 to about 20 percent by weight of the following, alone or in combination: phosphatidyl choline (derived from soy lecithin and supplied as Phospholipon 50 G from Rhone Poulenc Rorer); dioleoyl phosphatidylcholine; phoshatidylglycerol; dioleoylphosphatidylglycerol; dimyristoylphosphatidylcholine; dipalmitoylphosphatidylcholine; phosphatidylethalolamines; phosphatidylserines; or sphingomyelins; or other sources of phospholipids as those from purified Milk Fat Globule Membrane; glycerolesters; poly glycerol esters; or ethoxylated castor oil.

4. About 15 to about 30 percent by weight of the following, alone or in combination: hexanol; ethanol; butanol; heptanol; 2-methyl-1-pentanol; various ketone solvents that would be acceptable in foods such as methyl ethyl ketone, acetone and others; propylene glycol; and certain ester solvents such as ethyl acetate.

5. About 20 to about 40 percent by weight of the following, alone or in combination: modified starch such as Capsul™ Starch from National Starch, Inc.; methylcellulose; hydroxypropyl methylcellulose; hydroxyethylcellulose; hydroxypropylethylcellulose; pectin; gum arabic; gelatin; or other polymeric matrix-forming preparation known to those skilled in the art, soluble in water and, suitable for spray drying.

6. About 0.5 to about 35 percent by weight of the following, alone or in combination: aerosil 200; or any other flow enhancing excipient from silica, or related salt, known to those skilled in the art.

6.2. EXAMPLE 2: DETAILED LIST OF PRODUCTION STEPS USED FOR THE MANUFACTURE OF PROCESSED DIM ("P-DIM")

1. 6.75 kg of TPGS was heated just beyond its melting point with constant stirring in a heated vessel ("First vessel").

2. 9.38 kg of hexanol and 9.83 kg of jet milled DIM were added to the first vessel and the mixture stirred to a uniform suspension at 70° C. 1.4 kg of phosphatidyl choline was then added.

3. In a second larger vessel, 185 L of water and 10.7 kg of starch were thoroughly mixed with a Cowles blade. This mixture was neutralized to pH 7 with a small amount of sodium carbonate and then heated to 75° C. and stirred for 1 hour.

4. The contents of the first vessel was added to the starch mixture in the second larger vessel and thoroughly mixed with a homogenizing rotor/stator type mixer at moderate speed for 15 minutes.

5. The mixture from step 4 was spray dried with a small amount (approximately 0.5%) of hydrophilic silica to provide a free flowing powder of finely dispersed microparticles containing the co-precipitated TPGS, phosphatidyl choline and DIM in an amorphous, non-crystalline structure.
6. The flowable powder product was collected and stored in evacuated foil sacks, after de-aerating and flushing with nitrogen.
7. Analysis of presence of unchanged dietary ingredient, revealed about 30 to about 33 percent by weight of DIM.

DIM prepared according to the process of Example 2 is referred to herein as "processed DIM", or "p-DIM".

For effective treatment, the above preparation is administered to a mammal in an approximate dose of from about 1.5 to about 12 mg per kg per day by oral administration. This administration is effective in adjusting the balance of estrogen metabolism to favor 2-hydroxyestrone and 2-methoxyestrone.

6.3. EXAMPLE 3: INGREDIENTS OF AN ABSORPTION ENHANCING FORMULATION FOR CHRYSIN OR OTHER FLAVONOID

Ingredient List:
1. Pure flavone, flavonol, flavanone, isoflavone, flavone dimer in microcrystalline form (about 10 to about 40% by weight) selected from the group consisting of: chrysin apigenin, kampferol, quercetin, morin, naringenin, genistein, biochanin A, daidzein, amentoflavone, ginkgetin, isoginkgetin.
2. About 10 to about 40 percent by weight of the following, alone or in combination: vitamin E succinate polyethylene glycol 1000; vitamin E succinate Polyethylene glycols with polyethylene glycol (with a molecular weight range of 400–2000); other polyethylene glycol esters such as those formed by fatty acids such as oleic acid or stearic acid; polyvinylpyrrolidones; polyvinylpolypyrrolidones; Poloxamer 188, Tweens; or Spans.
3. About 5 to about 20 percent by weight of the following, alone or in combination: phosphatidyl choline (derived from soy lecithin and supplied as Phospholipon 5OG from Rhone Poulenc Rorer); dioleoyl phosphatidylcholine; phoshatidylglycerol; dioleoylphosphatidylglycerol; dimyristoylphosphatidylcholine; dipalmitoylphosphatidylcholine; phosphatidylethalolamines; phosphatidylserines; or sphingomyelins; or other sources of phospholipids as those from purified Milk Fat Globule Membrane; glycerolesters; poly gylcerol esters; or ethoxylated castor oil.
4. About 15 to about 30 percent by weight of the following, alone or in combination: hexanol; ethanol; butanol; heptanol; 2-methyl-l-pentanol; various ketone solvents that would be acceptable in foods such as methyl ethyl ketone, acetone and others; propylene glycol; and certain ester solvents such as ethyl acetate.
5. About 20 to about 40 percent by weight of the following, alone or in combination: modified starch such as Capsul™ Starch from National Starch, Inc.; methylcellulose; hydroxypropyl methylcellulose; hydroxyethylcellulose; hydroxypropylethylcellulose; pectin; gum arabic; gelatin; or other polymeric matrix-forming preparation known to those skilled in the art, soluble in water and, suitable for spray drying.
6. About 0.5 to about 35 percent by weight of the following, alone or in combination: aerosil 200; or any other flow enhancing excipient from silica, or related salt, known to those skilled in the art.

6.4. EXAMPLE 4: MANUFACTURE OF AN ABSORPTION ENHANCING PREPARATION FOR CHRYSIN ("P-CHRYSIN")

Manufacture of an absorption enhancing formulation for chrysin.
1. 6.5 kg of TPGS was heated just beyond its melting point with constant stirring in a heated vessel ("First vessel").
2. 19.5 kg of propylene glycol and 7.5 kg of jet milled chrysin were added to the first vessel and the mixture stirred to a uniform suspension at 80OC. 0.5 kg of phosphatidyl choline was then added.
3. In a second larger vessel, 75 L of water and 9.5 kg of starch were thoroughly mixed with a Cowles blade. Then 1 kg of sodium deoxycholate was added and mixed with the water and starch. This mixture was neutralized to pH 7 with a small amount of sodium carbonate and then heated to 75° C. and stirred for 1 hour.
4. The contents of the first vessel was added to the starch mixture in the second larger vessel and thoroughly mixed with a homogenizing rotor/stator type mixer at moderate speed for 15 minutes.
5. The mixture from step 4 was spray dried with a small amount (approximately 0.5%) of hydrophilic silica to provide a free flowing powder of finely dispersed microparticles containing the co-precipitated TPGS, phosphatidyl choline and DIM in an amorphous, non-crystalline structure.
6. The flowable powder product was collected and stored in evacuated foil sacks, after de-aerating and flushing with nitrogen. 7. Analysis of presence of unchanged dietary ingredient, revealed about 25 to about 30 percent by weight of chrysin.

Chrysin prepared according to the process of Example 4 is referred to herein as "processed chrysin", or "p-chrysin".

The method by which the above preparation, is administered to an animal in an approximate dose of from about 3 to about 30 mg/kg/day by oral administration is useful in adjusting the balance of estrogen metabolism by limiting the activity of the aromatase CYP enzyme system. This reduces the conversion of androstenedione to estrogen.

6.5. EXAMPLE 5: MANUFACTURE OF AN ABSORPTION ENHANCING FORMULATION OF BEE POLLEN

Bee pollen was obtained from a prefered source (C. C. Pollen Co., Phoenix, Arizona) and sustituted for the pure chrysin used in the manufacture of processed chrysin. The bee pollen was wet-milled to reduce particle size and crush pollen grains. From this point it was treated exactly as the pure chrysin and manufacturing steps as for processed chrysin were followed.

Bee pollen prepared according to the process of Example 4 is referred to herein as "processed-bee pollen", or "p-pollen".

For effective treatment, the above preparation is administered to a mammal in an appoximate dose of from about 5 to about 30 mg per kg per day by oral administration. This administration is effective in inducing hepatic CYP enzymes and specifically inhibiting the CYP aromatase enzyme.

6.6. EXAMPLE 6: PREPARATION OF AN ABSORPTION ENHANCING FORMULATION OF THE COMBINATION OF PROCESSED DIM (P-DIM), PROCESSED CHRYSIN (P-CHRYSIN), *URTICA DIOICA*, AND GRAPEFRUIT CONCENTRATE FOR IMPROVING MALE HEALTH AND THE WELL-BEING OF THE PROSTATE GLAND

With particulate preparations of and prepared according to the above steps the following dry ingredients are combined according to the following mg ratios, along with suitable excipients, binders and flow enhancing agents for encapsulating or tableting:

| | |
|---|---|
| P-DIM ™ | 150–300 mg |
| P-chrysin | 300–1500 mg |
| Urtica dioica extract | 300–600 mg |
| Grapefruit juice concentrate | 300–600 mg |

Alternatively, the above preparation may be prepared in a gelcap form with the addition of pygeum africanum, lycopene, vitamin D and zinc salts, suspended in a suitable carrier such as pumpkin seed oil.

For effective treatment, from one to three of the above tablets or capsules is administered once a day to a mammal orally.

6.7. EXAMPLE 7: PREPARATION OF AN ABSORPTION ENHANCING FORMULATION OF THE COMBINATION OF PROCESSED DIM (P-DIN), SOY ISOFLAVONE CONCENTRATE, SAW PALMETTO CONCENTRATE, GREEN TEA EXTRACT AND GRAPEFRUIT CONCENTRATE FOR IMPROVING HORMONAL BALANCE IN WOMEN

Manufacture of an absorption enhancing formulation of the combination of p-DIM, phytoestrogen concentrate and grapefruit juice concentrate is useful for improving general health and the well-being of breast and uterine tissue in women.

Ingredients include the following:

1. Phytoestrogen concentrate is obtained from a concentrated extract of soy beans containing the isoflavones genistein, daidzein and lignans in significant levels by a suitable extraction technique. Such an aqueous extraction in dilute alkali is exemplified by the commercially available powdered product, Genista by Natus, Inc.
2. With particulate preparations of p-DIM, phytoestrogen concentrate, green tea extract and grapefruit juice concentrate, the following dry ingredients are combined according to the following mg ratios, along with suitable excipients, binders and flow enhancing agents for encapsulating or tableting:

| | |
|---|---|
| P-DIM | 150–300 mg |
| Phytoestrogen concentrate | 300–600 mg |
| Green tea extract | 300–600 mg |
| Saw Palmetto concentrate | 300–600 mg |
| Grapefruit juice concentrate | 200–1,000 mg |

The method of treatment by which 1 to 6 capsules or tablets per day is administered orally to a woman.

6.8. EXAMPLE 8: PREPARATION OF AN ABSORPTION ENHANCING FORMULATION OF THE COMBINATION OF PROCESSED DIM, PROCESSED CHRYSIN, SAW PALMETTO CONCENTRATE, GREEN TEA EXTRACT, *URTICA DIOICA* EXTRACT AND GRAPEFRUIT JUICE CONCENTRATE FOR IMPROVING PHYSICAL CONDITIONING

With particulate preparations of p-DIM, p-chrysin and *Urtica dioica* prepared according to the above steps the following dry ingredients are combined according to the following mg ratios, along with suitable excipients, binders and flow enhancing agents for encapsulating or tableting:

| | |
|---|---|
| P-DIM | 150–300 mg |
| P-chrysin | 300–1500 mg |
| Saw Palmetto concentrate (4:1) | 300–600 mg |
| Urtica dioica extract | 300–600 mg |
| Green tea extract | 300–600 mg |
| Grapefruit juice concentrate | 300–600 mg |

The method of treatment by which 1 to 6 capsules or tablets per day is administered orally to a human with a small amount of fatty food and water.

6.9. EXAMPLE 9: EVIDENCE FOR ENHANCED ABSORPTION OF PROCESSED DIM IN ANIMALS

The absorption enhancing effect of the DIM microencapsulation process (producing p-DIM) was demonstrated in an experiment with rats. Mature male and female Sprague Dawley rats were fed either crystalline DIM or processed DIM. After 3 days, the rats were sacrificed and their livers harvested. Following isolation of liver microsomes, CYP enzymes S were assayed by Western Blots and CYP 1A1/1A2 was shown to be up to 11.4 times greater after feeding processed DIM than crystalline DIM. The procedure and results are as follows:

Groups of Sprague-Dawley rats were gavage fed crystalline DIM or processed DIM suspended in methylcellulose at a dose of 100 mg per kg for 3 consecutive days. After sacrifice, livers were perfused with saline solution and processed to isolate the microsomal fraction. Comparative enzyme induction was measured in microsomes with antibodies against total cytochrome (CYP) enzymes and specific CYP 1A1/1A2 enzymes. Results are as follows, expressed as percent of control level. In the CVP1A1/1A2 assay a 3.9 times advantage of processed DIM over crystalline DIM was shown in males and a 11.4 times advantage of processed DIM over crystalline DIM was shown in females.

| | Cytochrome Assayed DIM Formulation | Percent of Control (p-DIM over crystalline DIM) | |
|---|---|---|---|
| I. | Total CYP (nmol/mg protein) | | |
| | | males | |
| | crystalline | 140% | |
| | | males | |
| | P-DIM | 224% | (1.6 times) |
| II. | CYP 1A1/1A2 (densitometry units) | | |
| | | males | |
| | crystalline | 462% | |
| | | males | |
| | P-DIM | 1,831% | (3.9 times) |

-continued

| Cytochrome Assayed DIM Formulation | Percent of Control (p-DIM over crystalline DIM) | |
|---|---|---|
| crystalline | females 232% | |
| P-DIM | females 2,663% | (11.4 times) |

6.10. EXAMPLE 10: EVIDENCE THAT DIM MUST BE INCORPORATED IN PROCESSED FORM TO HAVE INCREASED BIOAVAILABILITY IN ANIMALS

A second experiment in animals was performed to demonstrate the advantage of the microencapsulation technology and its function as a nutrient delivery system. The bioavailability of processed DIM was compared to crystalline DIM co-administered with "blank" TPGS/phosphatidyl particles to demonstrate the need for microencapsulation processing to gain absorptive advantage. CYP enzyme induction was again used as a bio-marker of bioavailability.

The study compared the enzyme induction resulting from exposure of female rats to crystalline DIM, I3C and processed DIM at relevant doses in the feed. Levels of CYP 1A1/1A2 and 1B1 were measured in uterine and hepatic microsomes as a surrogate end point of uptake and bioavailability.

A total of 30 Sprague-Dawley female rats weighing approximately 200 gms were treated as follows:
1. 5–7 day acclimatization in group cages, feeding on AIN76A minimally inducing diet.
2. 3 days feeding on same feed mixed with 7 different combinations of dietary indoles.
3. Sacrifice of animals on about day 10. Harvesting of livers and uteri following perfusion of abdominal organs to remove blood.
4. Processing of organs to obtain CYP enzyme rich microsomal fraction.
5. Immunoblot determination of levels of specific CYP enzymes by standard means using existing CYP antibodies.

Microsomes from the following groups were assayed:

| Group | N | Feed | Purpose/Special Treatment |
|---|---|---|---|
| 1. Control | 3 | AIN76A plain | Neg |
| 2. Control/TCDD (Dioxin) by gavage | 3 | AIN76A plain | Pos |
| 3. | 3 | DIM low 2 mg/kg/day | DIM crystalline |
| 4. | 3 | DIM high 10 mg/kg/day | DIM crystalline |
| 5. | 3 | P-DIM low 6.8 mg/kg/day | Compare DIM |
| 6. | 3 | P-DIM high 34 mg/kg/day | Compare DIM |
| 7. | 3 | I3C low 5 mg/kg/day | Compare I3C |
| 8. | 3 | I3C high 25 mg/kg/day | Compare I3C |
| 9. | 3 | Placebo TPGS 34 mg/kg/day | Check TPGS |
| 10. | 3 | TPGS 6.8 mg/kg/day and DIM 2 mg/kg/day | |

Organ weight was obtained at necropsy. Specific CYP enzyme levels were compared based on standardized densitometry units. Results demonstrated clear advantage of processed DIM over crystalline DIM co-administered with TPGS. Results expressed as densitometry units indicating uptake of indole and degree of enzyme induction are listed according to the above groups:

| Group | N | Form of DIM | Densitometry Units |
|---|---|---|---|
| 1. | 3 | Control | 0 |
| 2. | 3 | TCDD (Dioxin) (positive control) | 251.7 |
| 3. | 3 | DIM low 2 mg/kg/day | 0 |
| 4. | 3 | DIM high 10 mg/kg/day | 0 |
| 5. | 3 | P-DIM low 6.8 mg/kg/day | 0 |
| 6. | 3 | P-DIM high 34 mg/kg/day | 38.2 |
| 7. | 3 | I3C low 5 mg/kg/day | 0 |
| 8. | 3 | I3C high 25 mg/kg/day | 5.1 |
| 9. | 3 | Placebo TPGS 34 mg/kg/day | 0.8 |
| 10. | 3 | TPGS and DIM crystals | 2.5 |

Since p-DIM is 34% crystalline DIM by weight, an equivalent mg amount of DIM was delivered in group 4 (DIM high) and group 6 (p-DIM high).

These results demonstrate the increase in bioavailabilty of p-DIM over crystalline DIM and the requirement that DIM be present in processed microparticulate form as in p-DIM in order to have such increased bioavailabilty.

6.11. EXAMPLE 11: EVIDENCE THAT DIM MUST BE INCORPORATED IN PROCESSED FORM TO HAVE INCREASED BIOAVAILABILITY IN HUMANS

Since the CYP inductive effect of dietary indoles is directly reflected by changes in the pattern of estrogen metabolism, collection of urine and quantitative analysis for the presence of key metabolites is a reliable surrogate endpoint for CYP enzyme status. This approach has been developed as a testing approach by Immunacare, Inc. Its Estratest™ elisa immunoassay for 20 H and 160 H estrone in urine has been utilized in assessing the bioavailability of p-DIM. This test provides a quantitative measure of 20 H estrone and 160 H estrone in ng/ml of first morning urine. These are the metabolites generated from CYP 1A1/1A2 cytochrome enzymes. From this quantification, a 20 H/160 H ratio is calculated. The Estratest™ was first used to replicate the evidence that p-DIM provided increased bioavailability over crystalline DIM in humans as was shown in animals. Crystalline DIM or p-DIM was administered to human subjects for various periods at various doses. Before and after urine collections were made and analyzed by elisa assay for quantities and ratios of 20 H versus 160 H estrone. These are the metabolites generated from CYP 1A1/1A2 enzymes. Results showed clear increases in the 20 H/160 H ratio.

| Individual | Dose of DIM % Increase of 2OH/16OH Ratio | Form of DIM |
|---|---|---|
| D.F. | 100 mg/day 0% | crystalline |
| M.Z. | 300 mg/day 0% | crystalline |
| D.F. | 50 mg/day 38% | p-DIM |
| M.Z. | 200 mg/day 71% | p-DIM |

Secondly, there is evidence for enzyme induction at progressively lower doses of processed DIM given for periods of at least one week assessed by before and after 20

H/16α H ratios. This series of dose-ranging studies confirmed the oral bioavailability of processed DIM at dosages below one mg/kg of body weight since many of the subjects tested weighed 70+kg. These results demonstrate bioavailability from the processed DIM formulation at a dosage level less than that demonstrated in the only animal feeding study with DIM which showed no hepatic enzyme induction when animals were fed one mg/kg of DIM in corn oil. Thus, enhanced bioavailability of p-DIM over crystalline DIM is supported.

| Individual | Dose of DIM<br>% Increase of<br>2OH/16OH Ratio | Form of DIM |
|---|---|---|
| E.C. | 300 mg/day<br>235% | p-DIM |
| M.W. | 200 mg/day<br>67% | p-DIM |
| C.C. | 200 mg/day<br>39% | p-DIM |
| K.K | 100 mg/day<br>318% | p-DIM |
| S.S. | 100 mg/day<br>15% | p-DIM |
| P.S. | 100 mg/day<br>40% | p-DIM |
| E.Z. | 75 mg/day<br>4% | p-DIM |
| M.F. | 75 mg/day<br>4% | p-DIM |
| K.W. | 75 mg/day<br>79% | p-DIM |
| M.W. | 50 mg/day<br>66% | p-DIM |
| H.B. | 50 mg/day<br>37% | p-DIM |
| M.S. | 50 mg/day<br>158% | p-DIM |

6.12. EXAMPLE 12: EVIDENCE THAT PROCESSED CHRYSIN PROMOTES ENHANCED ABSORPTION

The analytic technique of gas chromatography linked to mass spectrometry is able to identify and quantify all molecular species of steroid metabolites excreted in urine. A predigestion step with glucuronidase enzyme has been standardized to break down steroid glucuronide metabolites and thus produce a "steroid metabolite profile." This technique was used to demonstrate the shifts in estrogen metabolism resulting from dietary supplementation with bioavailable chrysin and chrysin in combination with bioavailable DIM. An experiment in humans was conducted to demonstrate the absorption promoting action of processed chrysin. The only previously published study for oral bioavailability of a flavonoid in humans failed to demonstrate any absorption.

To test the bioavailability of microparticulate chrysin in association with TPGS (p-chrysin), 24-hour urine collections were made in human subjects before and after the administration of a daily dose of 1.5 gms/day of p-chrysin. After one week of administration, a second 24-hour urine sample was collected. The analytical method for the determination of the urinary estrogen/androgen profile was based on capillary gas chromatography-mass spectrometry (GC/MS) in selected ion monitoring mode. (Johannessen, D. C., Adlecreutz, H., Fotsis, T, and Lonning, P. E., "Plasma and urinary oestrogens in breast cancer patients on treatment with 4-hydroxyandrostenedione", British J. of Cancer, 68, p. 393–398, 1993.) The following urinary steroid metaboilites were determined: 2-Hydroxyestrone, 4-Hydroxyestrone, 2-Hydroxyestradiol, 16-Hydroxyestrone, 16-Hydroxyestradiol, Estrone, Estradiol, Androstenedione, 4-androstenedione, testosterone, dihydrotestosterone, 5-androstenedione, and androsterone.

Results showed a reduction in estrone metabolites and an increase in metabolites of androstenedione, confirming inhibition of aromatase.

6.13. EXAMPLE 13: EVIDENCE THAT PROCESSED DIM, PROCESSED CHRYSIN AND URTICA DOICA PRODUCE A BENEFICIAL PATTERN OF STEROID METABOLISM IN HUMANS

Using the gas chromatography-mass spectrometry technique, a further experiment was performed with human volunteers to demonstrate the combined effect of processed DIM, processed chrysin and *Urtica Dioica* extract. A 24-hour urine sample was obtained before and after dosage with 1.5 gms/day of p-chrysin, 225 mg/day of p-DIM, and 300 mg/day *Urtica Dioica* extract. After one week of administration, a second 24-hour urine sample was collected. Analysis of urine samples was performed by GC/MS techniques as decribed in example 12.

Quantitative analysis of steroid metabolites revealed a marked decrease in estrogenic metabolites and a shift in estrone metabolites to favor 2α H estrone. These results demonstrate that the combination of p-chrysin, p-DIM, and urtica extract have additive effects when used as dietary supplements in humans. The combined effect of the phytochemicals through induction of estrogen hydroxylation and aromatase inhibition produced a unique and characteristic shift in urinary steroid metabolites.

In conclusion, new technology has been described which provides for the oral delivery of newly synthesized natural substances for use as dietary supplements. The formulations are unique since neither DIM nor chrysin has previously been available in sufficient quantities to permit such use. The new formulations overcome the problems of low solubility of the natural substances. The formulations thus provide for new methods of adjusting steroid metabolism in treated mammals. The formulation process has involved the development of novel techniques in the formation of microdispersions of the active substances. The technology of microdispersion formation has been refined to allow the formation of smaller and more stable microparticles of DIM and other chemopreventative phytochemicals. This technology has provided a novel delivery system for enhancing oral absorption of various, poorly water-soluble nutrients or drugs.

Although the invention is described in detail with reference to specific embodiments thereof, it will be understood that variations which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

Various publications are cited herein, the disclosures of which are incorporated by reference in their entireties.

What is claimed is:

1. A process for the preparation of a composition comprising the steps of:
   a. beating one or more solubilizing emulsifiers selected from the group consisting of vitamin E succinate polyethylene glycol 1000, polyvinylpyrrolidone, polyoxyethylene stearate, sodium cholate, deoxycholate and taurocholate;

b. adding to the product of step (a) one or more solvents and one or more surfactant phospholipids selected from the group consisting of phosphatidyl choline, dioleoyl phosphatidyl choline, phosphatidylglycerol, dioleoylphosphatidylglycerol, dimyristoylphosphatidylcholine, dipalitoylphosphatidyicholine, phosphatidylethanolamine, phosphatidylserine and sphingomyelin to produce a solution;

c. dissolving in the solution of step (b) one or more hydrophobic phytochemicals selected from the group consisting of diindolylmethane (3,3'-diindolylmethane), linear tri-indole([2-(indol-3-ylmethyl)-indol-3yl]indol-3-ylmethane), cyclic tri-indole (5,6,11,12,17,18-hex-hydrocyclononal [1,2-b:4,5-b':7,8-b]: triindole), and linear di-indole (1(3-hydroxymethyl)indolyl-3indolymethane, chrysin (5,7-dihydroxyflavone), tectochlrysin (5-hyroxy,7-methyletherflavone), nepetin (5,3',4'-trihydroxy-6-methoxyflayone), tangeretin (5,6,7,8,4'-pentamethoxyflavone), tricetin (5,7-dihydroxy-3',5'-trimethoxyflavone), tricin (5,7,4'trihydroxy-3',5'-dimethoxyflavone), amentoflavone, pinocembrin (5,7-dihydroxyflavanone), narigenin (5,7,4'trihydroxyflavanone), biochanin A, genistein, daidzein, propolis and bee pollen;

d. adding to the solution of step (c) a solution containing one or more encapsulators selected from the group consisting of starch, gelatin, methylcellulose, hdroxypropyl methylcellulose, hydroxyethylcellulose, hvdroxypropylethylcellulose, pectin and gum arabic;

e. mixing the solution produced in step (d) to produce a microdispersion with a particle size of 5 microns or less; and f. spray drying the resulting mixture to leave a solid hydrophobic phytochemical composition;

wherein the one or more emulsifiers comprise about 10 to about 40 percent by weight, the one or more solvents comprise about 1 5 to 30 percent by weight, the one or more surfactant phospholipids comprise about 5 to about 20 percent by weight, the one or more phytochemicals comprise about 10 to 40 percent by weight, and the one or more encapsulators comprise about 20 to 40 percent by weight of the microdispersion of step (e).

2. The process of claim 1 wherein said one or more solvents is selected from the group consisting of hexanoi, ethanol, butanol, heptanol, 2-methyl-1-pentanol, methyl ethyl ketone, acetone, propylene glycol, and ethyl acetate.

3. The process of claim 1 wherein said particle size is 2 microns or less.

4. The process of claim 1 wherein said particle size is 1 micron or less.

5. The process of claim 1 wherein said indole is diindolylmethane.

6. The process of claim 1 wherein said flavonoid is chrysin.

7. The process of claim 1 wherein said flavonoid is bee pollen.

8. A composition prepared according to the process of claim 5.

9. A composition prepared according to the process of claim 6.

10. A composition prepared according to the process of claim 7.

11. A method of adjusting the relative amounts of estrogen metabolites in a human comprising administering to said human an amount of the composition of claim 5 effective to increase the 20 H estrone to 160 H estrone ratio of said human.

12. A method of increasing the 20 H estrone to 160 H estrone ratio in a human comprising administering to said human an amount of the composition of claim 8 effective to induce the activity of CYP 1A1 or 1A2 enzymes of said human.

13. A method of adjusting the amount of testosterone or testosterone metabolites to estrogen or estrogen metabolites in a human comprising administering to said human an amount of the composition of claim 6 effective to increase the ratio of testosterone or testosterone metabolites to estrogen or estrogen metabolites in said human.

14. A method of adjusting the amount of testosterone in a human comprising administering to said human an amount of the composition of claim 6 effective to increase the amount of testosterone in said human.

15. A method of adjusting the amount of estrogen or estrogen metabolites in a human comprising administering to said human an amount of the composition of claim 6 effective to decrease the amount of estrogen or estrogen metabolites in said human.

16. A process for the preparation of a composition comprising the steps of:

a. heating one or more solubilizing emulsifiers selected from the group consisting of vitamin E succinate polyethylene glycol 1 000, polyvinylpyrrolidone, polyoxyethylene stearate, sodium cholate, deoxycholate and taurocholate;

b. adding to the product of step (a) one or more solvents and one or more surfactant phospholipids selected from the group consisting of phosphatidyl choline, diolcoyl phosphatidyl choline, phosphatidylglycerol, dioieoylphosphatidylglycerol, dirnyristoylphosphatidylcholine, dipalitoylphosphatidylcholine, phosphatidylethanolamine, phosphatidylserine and sphingomyelin to produce a solution;

c. adding to solution of step (b) one or more phytochemicals selected from the group consisting of *Urtica dioica* and *Urtica dioica* extract;

d. adding to the solution of step (c) a solution containing one or more encapsulators selected from the group consisting of starch, gelatin, methylcellulose, hydroxypropyl methylcellulose, hydroxyethylcellulose, hydroxypropylethylcellulose, pectin and gum arabic;

e. mixing the solution produced in step (d) to produce a microdispersion with a particle size of 5 microns or less; and f. spray drying the resulting mixture to leave a solid hydrophobic phytochemical composition;

wherein the one or more emulsifiers comprise about 10 to about 40 percent by weight, the one or more solvents comprise about 15 to 30 percent by weight, the one or more surfactant phospholipids comprise about 5 to about 20 percent by weight, the one or more phytochemicals comprise about 10 to 40 percent by weight, and the one or more encapsulators comprise about 20 to 40 percent by weight of the microdispersion of step (e).

17. The process of claim 16 wherein said one or more solvents is selected from the group consisting of hexanol, ethanol, butanol, heptanol, 2-methyl-1-pentanol, methyl ethyl ketone, acetone, propylene glycol, and ethyl acetate.

18. The process of claim 16 wherein said particle size is 2 microns or less.

19. The process of claim 16 wherein said particle size is 1 micron or less.

20. A composition prepared according to the process of claim 16.

21. A method of adjusting the amount of testosterone or testosterone metabolites relative to estrogen or estrogen metabolites in a human comprising administering to said human an amount of the composition of claim 20 effective to increase the ratio of testosterone or testosterone metabolites to estrogen or estrogen metabolites in said human.

22. A method of adjusting the amount of testosterone in a human comprising administering to said human an amount of the composition of claim 20 effective to increase the amount of testosterone in said human.

23. A method of adjusting the amount of estrogen or estrogen metabolites in a human comprising administering to said human an amount of the composition of claim 20 effective to decrease the amount of estrogen or estrogen metabolites in said human.

24. A method of increasing the bioavailability in a human of the composition of claim 20 by co-administering grapefruit juice, grapefruit juice concentrate, or grapefruit concentrate with the composition of claim 20 in an amount effective to increase the absorption of the composition of claim 20.

25. A composition prepared according to the process of claim 1.

26. A method of increasing the bioavailability in a human of the composition of claim 25 by co-administering to said human grapefruit juice, grapefruit juice concentrate, or grapefruit concentrate with the the composition of claim 25 in an amount effective to increase the absorption of the the composition of claim 25.

27. A method of increasing the bioavailability in a human of the composition of claim 8 by co-administering to said human grapefruit juice, grapefruit juice concentrate, or grapefruit concentrate with the composition of claim 8 in an amount effective to increase the absorption of the composition of claim 9.

28. A method of increasing the bioavailability in a human of the composition of claim 12 by co-administering to said human grapefruit juice, grapefruit juice concentrate, or grapefruit concentrate with the composition of claim 9 in an amount effective to increase the absorption of the composition of claim 9.

* * * * *